United States Patent [19]

Guesdon et al.

[11] Patent Number: 5,691,138
[45] Date of Patent: Nov. 25, 1997

[54] **NUCLEOTIDE SEQUENCES WHICH HYBRIDIZE SPECIFICALLY WITH A *CAMPYLOBACTER JEJUNI* GENOMIC NUCLEIC SEQUENCE**

[75] Inventors: Jean-luc Guesdon, Sevres; Véronique Stonnet, Asnieres, both of France

[73] Assignee: Institut Pasteur, Paris Cedex, France

[21] Appl. No.: 307,591

[22] PCT Filed: Jan. 31, 1994

[86] PCT No.: PCT/FR94/00122

§ 371 Date: Sep. 29, 1994

§ 102(e) Date: Sep. 29, 1994

[87] PCT Pub. No.: WO94/17205

PCT Pub. Date: Aug. 4, 1994

[30] Foreign Application Priority Data

Jan. 29, 1993 [FR] France ............................ 9300978

[51] Int. Cl.$^6$ ..................... C12Q 1/68; C07H 21/02; C07H 21/04
[52] U.S. Cl. ................... 435/6; 536/23.1; 536/24.3
[58] Field of Search ................... 435/6, 91.2, 23.1; 536/24.3

[56] References Cited

FOREIGN PATENT DOCUMENTS

WO86/04422  7/1986  WIPO.

OTHER PUBLICATIONS

Sambrook et al., "Molecular Cloning: A Laboratory Manual", Cold Spring Harbor Laboratory, NY (1989).
Choi et al. Nucleic Acids Research 16 (15) :7732 (1988).
Oyofo et al., J. of Clinical Microbiology 30 (10) : 2613–2619 (1992).
Tetsuo et al., Japaneese Patent Abstracts (Pub No. JP 3112498) 14 May 1991.
Jablonski et al., Nucleic Acids Research 14 (15): 6115–6128 (1986).
Chevrier et al., J. of Clinical Microbiology 27 (2) : 321–326 (1989).
Korolik et al., J. of Gemneral Microbiology 134 :521–529 (1988).

*Primary Examiner*—W. Gary Jones
*Assistant Examiner*—Ethan Whisenant
*Attorney, Agent, or Firm*—Oblon, Spivak, McClelland, Maier & Neustadt, P.C.

[57] ABSTRACT

The subject of the present invention is thus a nucleotide sequence which hybridizes specifically with a *Campylobacter jejuni* genomic nucleic acid sequence chosen from the nucleotide sequence SEQ ID No. 1, the nucleotide sequence SEQ ID No. 2 the sequences complementary to the latter, as well as the sequences differing therefrom by nutation, insertion, deletion or substitution of one or more bases, and which does not or virtually does not hybridize with nucleic acids from other Campylobacter species.

Fragments of this sequence can be used as specific primers for the amplification of sequences specific for *Campylobacter jejuni* and as nucleic probes specific for *Campylobacter jejuni* nucleic sequences.

The subject of the invention is also a method of detecting the presence of *Campylobacter jejuni* stains in a biological sample, as well a kit for carrying out the method.

15 Claims, 1 Drawing Sheet

FIG.1

NUCLEOTIDE SEQUENCES WHICH HYBRIDIZE SPECIFICALLY WITH A *CAMPYLOBACTER JEJUNI* GENOMIC NUCLEIC SEQUENCE

The present invention relates to a nucleic sequence specific for *Campylobacter jejuni* as well as to the applications of this sequence as nucleotide probe specific for the detection of *Campylobacter jejuni* sequences or fragments of this sequence as nucleotide primers for the amplification of *Campylobacter jejuni* DNA or RNA in a biological sample.

Campylobacter infections are widespread throughout the World, affecting both men and wild or domestic animals.

Although discovered at the beginning of the twentieth century, the bacteria currently called Campylobacter were for long ignored because their characteristics made their identification and their culture difficult. First isolated from the Ovidae and the Bovidae and called *Vibrio fetus* then, later, *Campylobacter fetus*, it was only from 1946 that the first cases of human campylobacterioses were described, but it was only from 1972, when selective media for Campylobacter started to be developed, that the importance of Campylobacter infections was able to be proved and recognized.

Since the naming of the type species *Campylobacter fetus*, about twelve other species and subspecies have been discovered, the exact number varying according to the authors and taxonomic methods, who often propose new classification criteria. Among these species, those most frequently encountered in human and/or animal pathology are *Campylobacter jejuni*, *Campylobacter coli* and *Campylobacter fetus*.

Currently, *Campylobacter jejuni* is considered as one of the most frequent causes of infectious diarrhoea in man.

The "national network for monitoring Campylobacter infections", set up in France in 1986, publishes each year an assessment setting out the principal epidemiological and clinical data for the cases reported. For the years 1988, 1989 and 1990 for example, it seems that the species most frequently implicated in these infections (from 60 to 75% of the cases analysed) was *C. jejuni*.

In the human species, the major symptom of intestinal *C. jejuni* infection is diarrhoea which, in the most serious cases, can cause severe water loss, which can be particularly dangerous for children and infants, who are very sensitive to dehydration. However, *C. jejuni* enteriris often remains without complications and the diarrhoeas can even cease spontaneously after one week. However, coprocultures may remain positive after a few weeks or even months, and, in 5 to 10% of cases, relapses can occur. Vigorous treatment and monitoring are therefore necessary, especially for immuno-suppressed individuals or individuals having serious diseases (AIDS, cirrhosis of the liver, cancer, leukaemia and the like), in whom Campylobacter can behave like opportunistic bacteria.

Other consequences of *C. jejuni* infections have also been described, although they are more rare or exceptional: mesenteric adenitis, cholecystitis, urinary infections, meningitis, septicaemias, erythema nodosum or Guillain-Barré syndrome and the like.

In animals, Campylobacter usually lives as commensals in the digestive tube of numerous species: bovines, ovines, pigs, poultry, wild birds, dogs and cats. These animals, diseased or healthy carriers, constitute a big reservoir of microbes, and therefore a high risk of contamination. In the case of obvious infections, in bovines and ovines, *C. jejuni* is known, since the first description in 1931, as being the cause of "cattle dysentery", which may have as a consequence, besides the effect on the cattle, the transmission to man through the spread of the microbes in the surroundings of the animals (land, water). Even for asymptomatic animals, "healthy carriers", the transmission to man can occur: either by direct contact with these animals or their excrement, or by consumption of contaminated foods or water (meats contaminated during their preparation and poorly cooked, unpasteurized milk, polluted water and the like).

From a prevention perspective, it is therefore important, both in man and in animals, to be able to identify the pathogen *C. jejuni* as early as possible, so as to prevent, by adequate measures, any contamination. This is particularly the case in the food industry where sterile conditions must be observed. It is also important in human pathology, in order to carry out proper monitoring of the patients treated following a *C. jejuni* infection, so as to avoid any new relapse.

Finally, in the case of declared infections, it is very important to properly identify the microbe which is responsible, and this rapidly after the onset of the disease, in order to be able to apply proper and effective treatment which would prevent the progression of the infection, or even the propagation of epidemics. Now, the identification of Campylobacter and the determination of the incriminated species is not easy. Indeed, their isolation requires special media and their conventional detection is currently done only after an enrichment by culturing for at least 48 hours. This is very long when a rapid diagnosis is necessary. Moreover, given that microbiological diagnosis is currently done by bacteriological and/or biochemical techniques which exploit phenotypic differences which exist between the different species, diagnostic errors can occur, especially when mutants appear for a given character. In the specific case of *C. jejuni* and *C. coli*, the sole differentiation criterion is the hydrolysis of hippurate (*C. jejuni* can hydrolyse it whereas *C. coli* cannot), and it sometimes happens that this distinction cannot be made because hippurate-negative *C. jejuni* strains exist (Hébert et al., J. Clin. Microbiol., 1984, 20, 138–140, Totten et al., J. Clin. Microbiol., 1987, 25, 1747–1752).

Approaches using molecular hybridization to identify the *C. jejuni* species have been proposed. However, these methods permit identification only after culturing, they are not sufficiently sensitive to detect this bacterium in biological samples. Thus, methods for the identification and classification of Campylobacter have been proposed, using either radioactive probes (Ng et al., Mol. Cell. Probes, 1987, 1, 233–243), or non-radioactive probes (Chevrier et al., J. Clin. Microbiol., 1989, 27, 321–326), but these methods use total genomic probes and necessitate an enrichment by culturing the pathogen to be detected, because the detection threshold is quite high, about $10^5$ bacteria (Chevrier et al., above).

Searches for nucleic probes specific for *C. jejuni* for the purpose of diagnosis of species, have been made by Picken et al. (Mol. Cell. Probes, 1987, 1, 245–259), Korolik et al. (J. Gen. Microbiol., 1988, 134, 521–529) and Zhou and Wang (Zbl. Bakt., 1989, 272, 186–190), but problems of specificity remain and the sequences of these potential probes have not been determined. Likewise, another probe "specific" for *C. jejuni*, consisting of an oligomer coupled to alkaline phosphatase and whose sequence has not been published, has been described (Jablonski et al., N.A.R., 1986, 14, No. 15), but its specificity has been tested only with respect to a fragment from *C. jejuni* and not against the entire genome of *C. jejuni* and of the other species of the genus Campylobacter.

Recently, one approach to identify *C. jejuni* by PCR has been described, using oligonucleotides chosen from the fla A gene from *C. coli* VC167 (Oyofo et al., J. Clin. Microbiol., 1992, 30, No. 10, 2613–2619); however, this method does not allow *C. jejuni* to be distinguished from *C. coli*.

The inventors have now isolated a nucleic sequence which can be used for the specific detection of the species *Campylobacter jejuni*.

The subject of the present invention is thus a nucleotide sequence which hybridizes specifically with a *Campylobacter jejuni* genomic nucleic acid sequence, characterized in that it is chosen from the nucleotide sequence SEQ ID No. 1, the sequence complementary to the latter, as well as the sequences differing therefrom by mutation, insertion, deletion or substitution of one or more bases.

The subject of the invention is also a nucleotide sequence containing all or part of the nucleotide sequence as defined above, especially a nucleotide sequence chosen from the nucleotide sequence SEQ ID No. 2, and the sequence complementary to the latter, as well as the sequences differing therefrom by mutation, insertion, deletion or substitution of one or more bases.

By "sequences differing therefrom by mutation, insertion, deletion or substitution of one or more bases", there is understood the sequences which hybridize with the sequence SEQ ID No. 1, SEQ ID No. 2 or their complementary sequences under the usual stringency conditions which are defined by SAMBROOK J., FRITSCH E. F. and MANIATIS T. (1989): Molecular Cloning: A Laboratory Manual, Ed. Cold. Spring Harbor Laboratory 9.47–9.62).

These conditions are determined from the medium stringency temperature Tm.

Preferably, the most advantageous sequences are those which hybridize within the temperature range (Tm—15° C.) to (Tm—20° C.).

The sequences in question advantageously contain at least 12 nucleotides.

The subject of the invention is also the products of amplification of a sequence as defined above.

The subject of the invention is also a cloning vector containing a nucleotide sequence as defined above.

The nucleotide sequences defined above may be DNA sequences or RNA sequences.

The exact size of the fragment of sequence SEQ ID No. 1 is 147 bp. This sequence is specific for the species *C. jejuni* and does not hybridize with 8 other representative species of the genus Campylobacter.

The fragment of sequence SEQ ID No. 2 has a length of 1189 bp and hybridizes very weakly with *Campylobacter coli*, but not with the other 7 Campylobacter species tested.

A search of the data bank "Genebank" and "EMBL" did not reveal any homology between, on the one hand, the sequences SEQ ID No. 1 and SEQ ID No. 2 and, on the other hand, the known DNA sequences.

The sequences SEQ ID No. 1 and SEQ ID No. 2, functionally equivalent parts or variants thereof, can be used in molecular hybridization techniques for the detection and identification of *Campylobacter jejuni*.

The functionally equivalent variants comprise sequences in which base pairs have been mutated, deleted, inserted or substituted, without the properties which are essential for the specificity of these fragments being affected.

The nucleotide sequences according to the invention have diagnostic and epidemiological applications in human or veterinary medicine, especially as nucleic probes specific for *Campylobacter jejuni* or as oligonucleotide primers for the amplification of a sequence specific for *Campylobacter jejuni*.

The probes according to the invention advantageously comprise at least 20 consecutive nucleotides among the sequences or the fragments of sequences mentioned above.

The probes are DNA probes or RNA probes.

The nucleotide sequences described in this invention can thus be used as probes to detect specifically and in a direct manner strains of *Campylobacter jejuni* in a biological sample and permit the detection of bacteria of the species *Campylobacter jejuni*, irrespective of the biotype to which these bacteria belong (there are 4 "Lior biotypes", called I, II, III and IV, which classify bacteria of the species *C. jejuni* according to their capacity to hydrolyse hippurate, to produce $H_2S$ and DNase I).

The oligonucleotide probes described also detect the subspecies *C. jejuni* subsp. *doylei*.

The oligonucleotide probes do not detect DNA from bacteria belonging to other genre which are likely to be present in the same biological sample of *C. jejuni*: *Bacteroides fragilis*, *Enterococcus faecalis*, *Enterococcus faecium* and *Streptococcus agalactiae*.

The unlabelled sequences can be used directly as probes, however the sequences are generally labelled with a radioactive element ($^{32}P$, $^{35}S$, $^{3}H$, $^{125}I$) or with a non-radioactive molecule (biotin, acetylaminofluorene, digoxigenin, 5-bromodeoxyuridine) in order to obtain probes which can be used for numerous applications.

In this latter case, it will be possible to use one of the labelling methods described in FR 2,422,956 and FR 2,518,755. The hybridization technique can be performed in various ways (Matthews, J. A. and Kricka, L. J., Anal. Biochem. 1988, 169, 1–25). The method most widely used consists in immobilizing the nucleic acid extracted from the *Campylobacter jejuni* cells onto a support (nitrocellulose, nylon, polystyrene and the like) and in incubating, under well-defined conditions, the immobilized target nucleic acid with the probe. After hybridization, the excess probe is removed and the hybrid molecules formed are detected by the appropriate method (measurement of the radioactivity, the fluorescence or the enzymatic activity linked to the probe and the like).

In another application, the nucleic acid probes described here can be used as capture probes. In this process, the probe is immobilized on a support and serves to capture by specific hybridization the target nucleic acid extracted from *C. jejuni*. If necessary, the solid support is separated from the sample and the duplex formed between the capture probe and the target nucleic acid is then detected by means of a second detection probe labelled with an easily detectable element.

When a sufficient quantity of *Campylobacter jejuni* nucleic acid can be extracted from samples to be analysed, the sequences described in the patent can be used to detect and identify the strains belonging to *Campylobacter jejuni* directly in these samples. In the opposite case, a rapid culture in liquid medium can be carried out before extraction of the nucleic acid from *Campylobacter jejuni*, or alternatively the small quantity of *Campylobacter jejuni* nucleic acid extracted from the sample can be subjected to an amplification technique such as for example the PCR technique.

The sequences SEQ ID No. 1 and SEQ ID No. 2 or the fragments obtained from these sequences can also be used to select oligonucleotide primers, especially for the PCR technique.

This technique requires the choice of pairs of oligonucleotides flanking the fragment which has to be amplified (Patent U.S. Pat. No. 4,683,202). These oligodeoxyribonucleotide or oligoribonucleotide primers advantageously have a length of between 18 and 30 and preferably 18 and 22 nucleotides. One of the two primers is complementary to the (+) strand of the template and the other primer is complementary to the (−) strand. It is important that these primers do not contain a secondary structure or a mutually complementary sequence. Moreover, the length and the sequence of each primer should be chosen so that the primers do not hybridize with other nucleic acids derived from prokaryotic or eukaryotic cells, in particular with the nucleic acids from Campylobacter not belonging to the species *jejuni* and with human DNA or RNA which may possibly contaminate the sample.

The amplimers selected as specific primers for the amplification of nucleic sequences from strains belonging to *Campylobacter jejuni* are chosen for example according to the method described by Griffais et al. (Nucleic Acids Res. 1991, 19, 3887–3891).

From the sequence SEQ ID No. 2, the inventors chose oligonucleotides in order to carry out a PCR test. Using these oligonucleotides, they obtained an amplification specific for *Campylobacter jejuni*, no amplification was visible with nucleic acid from other Campylobacter species.

A pair of primers which is most particularly preferred is represented by the oligonucleotides VS15 and VS16 derived from the sequence SEQ ID No. 2, of sequences:

Oligo VS15: 5' GAA TGA AAT TTT AGA ATG GGG 3'

Oligo VS16: 5' GAT ATG TAT GAT TTT ATC CTGC 3'

The amplified fragments can be identified after agarose or polyacrylamide gel electrophoresis, or after capillary electrophoresis or alternatively after a chromatographic technique (gel filtration, hydrophobic chromatography or chromatography on an ion exchanger). The specificity of the amplification can be checked by molecular hybridization using as probes the nucleotide sequences SEQ ID No. 1 or SEQ ID No. 2, fragments of the latter, plasmids containing these sequences or fragments of the latter, oligonucleotides complementary to these sequences or fragments of sequences or amplification products. These probes can be labelled or otherwise with radioactive elements or with non-radioactive molecules.

The subject of the present invention is also a method of detecting the presence of *Campylobacter jejuni* strains in a biological sample, characterized by the following steps:

i) bringing the biological sample into contact with a pair of oligonucleotide fragments called primers, as defined above, the nucleic acid contained in the sample having, where appropriate, being previously rendered accessible to the hybridization and under conditions permitting hybridization of the primers to the nucleic acid from the strains belonging to *Campylobacter jejuni*;

ii) amplifying the nucleic acid from the *Campylobacter jejuni* strains;

iii) detecting the amplification of nucleic acid fragments corresponding to the fragment flanked by the primers;

iv) optionally verifying the sequence of the amplified fragment, for example by hybridization of a specific probe, by sequencing or by restriction site analysis.

The limit of detection, in an aragose gel after PCR amplification, is one bacterium when 10-fold serial dilutions of a bacterial suspension of *C. jejuni* are subjected to the amplification.

The subject of the present invention is additionally a kit or box for detecting the presence of strains belonging to *Campylobacter jejuni* in a biological sample, characterized in that it comprises the following elements:

a pair of oligonucleotide fragments as defined above;

the reagents necessary for carrying out an amplification of nucleic acid from strains belonging to *Campylobacter jejun*;

optionally, a component which makes it possible to verify the sequence of the amplified fragment, more particularly a nucleic probe as defined above.

This kit contains more advantageously the labelled or non-labelled probe(s). These may be in solution or immobilized on a support. The kit may also contain the reagents necessary for the lysis of the bacteria and the extraction of the target nucleic acids, as well as the hybridization and washing solutions corresponding to the chosen method.

The subject of the invention is also the use of a nucleic probe as defined above as epidemiological tool, in molecular epidemiology, Indeed, if the specific fragment is present several times in the *C. jejuni* genome, its repetitiveness can serve as tool to locate and classify identical strains, and, obviously, to establish links as to their source and the propagation of the infection.

The invention is illustrated in greater detail in the following examples and in the accompanying Figure, representing the strategy for sequencing the sequence SEQ ID No. 2 (fragment VS 1):

EXAMPLE 1

Construction of the *C. jejuni* genomic library. Screening of the library and determination of the sequence of the specific fragment:

The genomic DNA from *C. jejuni* CIP (Pasteur Institute Collection) 70.2 is partially digested with the restriction endonuclease Hind III by reacting 0.06U of enzyme per µg of DNA in the buffer recommended by the supplier for 1 hour at 37° C. The genomic DNA thus digested is separated by electrophoresis on a 0.5% agarose gel. The fragments whose length is between 30 and 40 kb are electroeluted and precipitated in ethanol after phenol/chloroform (1/1) extraction.

The vector is the cosmid ref. pHC79 (provided by Boehringer). It is digested in the same manner and dephosphorylated in order to avoid any self-ligation.

The ligation is performed by mixing 700 ng of vector and 1.5 µg of DNA fragments of 30/40 kb, the mixture is left at 14° C. for 18 hours after having added 1 unit of T4 DNA ligase in an appropriate buffer.

The recombinant cosmids are encapsulated in vitro and used to transform the bacteria (*E. coli* HB 101). The transformed bacteria are incubated for 1 hour at 37° C. in LB medium, then plated on a selective Agar medium containing 25 µg/ml of ampillicin. The ampicillin-resistant colonies are all tested for their sensitivity to tetracycline (the 30/40 kb DNA fragment is inserted into the vector so as to inactivate the tetracycline (Tet) resistance gene and to conserve the ampicillin (Amp) resistance gene).

A mini preparation of DNA from the first 60 transformant colonies resistant to ampicillin (Amp$^r$) and sensitive to tetracycline (Tet$^s$) is performed according to the alkaline lysis technique. The DNA from these preparations is then digested with the restriction endonuclease Hind III, analysed by electrophoresis on a 0.8% agarose gel, and then transferred onto nylon filters. The DNA is irreversibly fixed by exposing to UV at 254 nm for 3 minutes.

These different filters are incubated for 16–18 hours at 65° C. in a 6X SSC buffer (1X SSC corresponds to 0.15M NaCl and 0.015M Na citrate) containing 10% dextran sulphate, a 5X concentrated Denhardt's solution (a 1X Denhardt's solution corresponds to 0.02% Ficoll, 0.02% polyvinylpyrrolidone and 0.02% bovine serum albumin), 10 mM EDTA, 0.5% SDS, 100 μg/ml of denatured salmon sperm DNA and genomic DNA, radiolabelled with $^{32}$P by "multipriming", one of the following three species: *C. jejuni* CIP 70.2, *C. coli* CIP 70.80 and *C. fetus* subsp. *fetus* CIP 5396.

After hybridization, the filters are washed for example for twice 10 minutes in 2X SSC at 65° C., once for 30 minutes in 2X SSC+0.1% SDS at 65° C., and finally once for 10 minutes in 0.1X SSC at 65° C. The filters, still wet, are subjected to autoradiography at −80° C. with an intensifying screen for 15 minutes to 3 days.

The results of these hybridizations made it possible to isolate a cosmid clone containing a fragment of about 1.2 kb called VS1. This fragment was cloned into a vector pUC18 (marketed by Boehringer) and prepared in a large quantity. The resulting plasmid was called pVS20.

The specificity of the fragment was verified as described in Example No. 2.

The fragment VS1 was cloned into the M13mp18 phage and sequenced according to the Sanger method using the sequencing kit "Sequenase 2.0" (United States Biochemia Corporation). Some parts of the fragment VS1 were sequenced directly in the plasmid pVS20, after alkaline denaturation of the two DNA strands. All the sequencing reactions were performed with $^{35}$S-labelled dATP.

Figure 1:
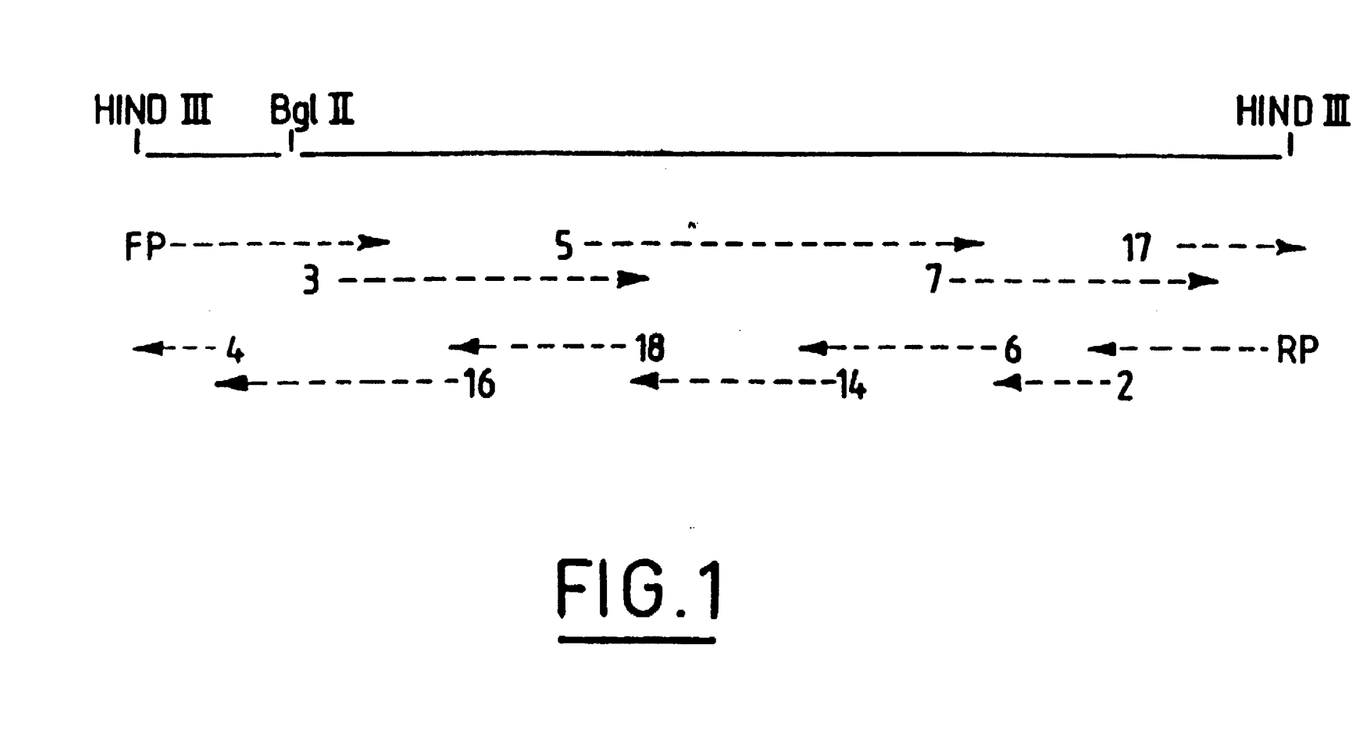

The diagram of the accompanying Figure represents the strategies followed for sequencing the fragment VS1, 2, 3, 4, 5, 6, 7, 14, 16, 17, 18 representing the different primers used for the sequencing, FP and RP being universal primers complementary to the DNA of pUC18 and M13mp18.

The entire sequence of the fragment is the sequence SEQ ID No. 2. Comparison between the databanks "Genebank" and "EMBL" and the 1189 nucleotides of the fragment VS1 thus determined reveals no significant homology with the sequences known today.

EXAMPLE 2

DNA analysis by the Southern technique, using as probes the nucleic acid sequences of the invention:

The list and the references of the bacteria used in this study are the following:

Campylobacter:
  *C. jejuni* CIP 70.2
  *C. coli* CIP 70.80
  *C. lari* CIP 102722
  *C. fetus* subsp. *fetus* CIP 5395
  *C. fetus* subsp. *venerealis* CIP 6829
  *C. hyointestinalis* C120
  *C. curvus* (Hospital for Children, Bordeaux)
  *C. sputorum* subsp. *sputorum* CCUG 9728
  *C. sputorum* subsp. *bubulus* CIP 53103
  *C. concisus* 18688
  *C. fecalis* CIP 12014
Non-Campylobacter:
  *Escherichia coli* HB101
  *Helicobacter pylori* CIP 101260
  *Salmonella typhimurium* CJ 53
  *A. cryaerophilus* CCUG 17801.

DNA from bacteria not belonging to the genus Campylobacter:

The DNA from these bacteria and from *C. jejuni* used as positive control was hydrolysed with the restriction enzyme Hind III, then the fragments were separated by agarose gel electrophoresis and transferred onto a nylon membrane Hybond-N. These different DNA fragments are analysed by molecular hybridization using as probe the fragment VS1 labelled with $^{32}$P according to the technique for the "Random primed DNA Labelling" kit (Boehringer). Autoradiography shows that the only species detected is *C. jejuni*. No hybridization is detectable on the DNAs from the non-campylobacterial species, even after 72 hours of exposure.

DNA from bacteria belonging to the genus Campylobacter, other than *C. jejuni*:

After culturing on an appropriate medium (5% sheep blood agar, Biomérieux), the Campylobacter species are treated in the following manner.

The bacteria from each Petri dish are harvested with 2 ml of TE-glucose buffer (25 mM Tris-HCl pH 8, 10 mM EDTA, 50 mM glucose), centrifuged for 5 minutes at 5000 g, the pellet is redispersed and washed with TE-glucose and then recentrifuged, the bacteria are resuspended in 100 μl of TE buffer (10 mM Tris-HCl pH 8, 1 mM EDTA) and the DNA is extracted according to the technique of Pitcher et al. (Lett. Appl. Microbiol., 1989, 8, 151–156). The DNAs thus extracted undergo a total digestion with the enzyme Hind III. The fragments obtained are then separated by electrophoresis on a 0.8% agarose gel in TAE before being transferred onto a nylon membrane according to the Southern technique.

The fragments transferred are analysed by molecular hybridization. In this example, the probes used were, separately, the fragment VS2 (of sequence SEQ ID No. 1) and the fragment VS3, obtained after hydrolysis of the fragment VS1 with the enzyme Bgl II. These two probes were labelled with $^{32}$P.

The probe VS2 detects specifically the DNA from *C. jejuni* and does not hybridize with the genomic DNAs from other Campylobacter species.

The probe VS3 also detects the DNA from *C. jejuni*, but also hybridizes very weakly with a DNA fragment situated on the *C. coli* genome. This crosshybridization was detectable only after 16 hours of exposure, whereas the DNA from *C. jejuni* is detectable after only 15 minutes of exposure.

The results as a whole lead to the conclusion that the probe VS1 (SEQ ID No. 2) detects specifically the DNA from *C. jejuni* among DNAs from bacteria of other genera, and that the fragment VS2 (SEQ ID No. 1) recognizes specifically *C. jejuni* in the case of an accurate identification within the genus Campylobacter.

EXAMPLE 3

Enzymatic amplification in vitro of the DNA from *C. jejuni* with the primers defined from the nucleic acid sequence which is the subject of the invention.

Choice of the primers:

It has been demonstrated that it is essentially the 3' end of the oligonucleotide primers which determine the specificity of the PCR (PCR Protocols, M. Innis et col., Academic Press Inc.). It is therefore important that this 3' region is perfectly specific for the target to be amplified.

Given that the Campylobacter genome has a very small percentage of guanine and cytosine (between 28 and 38% of G+C), it was considered that primers whose 3' end was rich in G+C could exhibit a high degree of specificity.

The inventors sought within the VS1 sequence, zones rich in G+C and which are present only once in VS1. It is from these regions that the sequence of the primers was oriented and completed so as to obtain a length of about 20 nucleotides.

Synthesis of the oligonucleotide primers:

The primers derived from the VS1 sequence, called oligoVS15 and oligoVS16, whose sequences are indicated above and having a length of 21 and 22 nucleotides respectively, were synthesized in an automated apparatus "Cyclone Plus" (millipore) based on the chemistry of phosphoramidites. After the synthesis, the oligonucleotide solution is transferred into a tube and incubated with concentrated ammonium hydroxide for 16 hours at 55° C. The oligonucleotide is precipitated with ethanol, then the pellet is washed with 70% ethanol and dried. Finally, the pellet is taken up in 1 ml of sterile distilled water. The concentration of each primer is determined using the spectrophotometer.

Amplification:

The amplification technique, for example enzymatic amplification in vitro (PCR), is carried out according to the procedure described by Saiki et al. (Science, 1988, 239, 487–491) using 1 µM of the oligonucleotides oligoVS15 and oligoVS16 and 30–100 ng of DNA from different Campylobacter strains with 0.5 unit of Taq polymerase in a buffer containing 25 mM KCl, 20 mM Tris-HCl pH 8.5, 1.5 mM $MgCl_2$, 200 µM deoxyribonucleotide triphosphates and 100 µg/ml of bovine serum albumin, the final reaction volume being 50 µ. The parameters for the PCR steps were chosen in the following manner: 5 minutes at 94° C., 1 minute at 60° C., 1 minute at 72° C., then (1 minute at 94° C., 1 minute at 60° C., 1 minute at 72° C.) 28 times and a final cycle 1 minute at 94° C., 1 minute at 60° C., 5 minutes at 72° C. Thirty cycles are thus carried out using an automatic apparatus. After the final cycle, the samples are maintained at 4° C. up to the analysis.

Electrophoretic analysis on an agarose gel of the amplified samples:

Ten µl of the amplified samples are deposited on a 2% agarose gel in a TBE buffer (0.04M Tris-borate, 0.001M EDTA) containing 1M g/ml of ethidium bromide. The amplified fragments are visualized under UV and the gels are photographed using a Polaroid 667 film.

The results obtained with, on the one hand, various DNAs from Campylobacter, on the other hand, various DNAs from bacteria not belonging to the genus Campylobacter, and the primers oligoVS15 and oligoVS16, were compared. The expected theoretical length of the fragment amplified with this pair of primers is 358 base pairs.

Only the DNA extracted from C. jejuni makes it possible to obtain such a fragment.

No amplified fragment of the expected size is visible when the DNA analysed is extracted from the following strains: C. coli, C. lari, C. fetus subsp. fetus, C. fetus subsp. venerealis, C. hyointestinalis, A. cryaerophilus, C. sputorum subsp. sputorum, C. sputorum subsp. bubulus, C. concisus, C. fecalis, E. coli, H. pylori, S. typhimurium, C. curvus, or human cells.

In the case of C. fetus subsp. fetus, a high-molecular weight fragment was amplified, but in a non-specific manner, because after transferring onto a nylon membrane, this fragment does not hybridize with the $^{32}P$-labelled VS1 probe.

Moreover, the technique for identification of C. jejuni by PCR which is described above was used to test 15 C. jejuni strains isolated from guinea fowls. The amplification was carried out after subculturing the strains and extracting the DNA. All the strains were identified as being C. jejuni, which is in agreement with the biochemical tests carried out beforehand.

Determination of the sensitivity of the PCR test

In order to determine the absolute threshold for detection of C. jejuni DNA by PCR with the pair of oligonucleotides described here, several 10-fold serial dilutions of a bacterial suspension of C. jejuni were subjected to the PCR amplification. The amplification comprises 40 cycles, the cycles being carried out under the conditions described above, and is performed after mixing the dilutions with an appropriate lysis buffer followed by a heat treatment (incubation for 15 minutes at 65° C., then for 10 minutes at 95° C.). The composition of the lysis buffer is the following: 10 mM Tris-HCl, 1 mM EDTA, pH 8 containing 0.5% Tween 20, 0.5% Nonidet-P40 and 500 µg/ml proteinase K.

A volume of 100 µl of each dilution, identical to that subjected to the lysis, was plated on a Petri dish containing a culture medium for Campylobacter, and the colonies were counted after incubating for 48 hours. Under these conditions, the detection limit was seven bacteria.

With the PCR method, by subjecting to amplification 10 µl of each dilution, the detection limit is statistically one bacterium (theoretical dilutions of $3.5 \times 10^7$ bacteria/100 µl to 3.5 bacteria/100 µl respectively, corresponding to dish counts of $2.5 \times 10^7$, $10^6$, $10^5$, $1.5 \times 10^4$, 560, 32, 7 and 0 bacteria in 100 µl respectively).

In conclusion, it is important to note that this pair of primers makes it possible to detect specifically the species C. jejuni, which suggests that isolates from patients and biological samples infected with C. jejuni can be identified, thus making the method usable in the field of clinical bacteriology and in veterinary medicine.

The method of detecting C. jejuni according to the invention can also be used to detect the presence of C. jejuni in foods (chicken escalope, beef, milk, water) with the aid of the oligonucleotide probes previously described.

In this case, the removal of coarse organic food debris by low-speed centrifugation is necessary before the lysis of the bacteria, in order to improve the results of the PCR test and to avoid possible false negatives due to inhibition of the amplification reaction.

We claim:

1. A purified nucleotide sequence which hybridizes specifically with a *Campylobacter jejuni* genomic nucleic acid sequence selected from the group consisting of:
    a nucleotide sequence of SEQ ID NO:1;
    a nucleotide sequence of SEQ ID NO:2;
    a nucleotide sequence fully complementary to SEQ ID NO:1;
    a nucleotide sequence fully complementary to SEQ ID NO:2;
    a nucleotide sequence which hybridizes with SEQ ID NO:1 under stringent conditions;
    a nucleotide sequence which hybridizes with a nucleotide sequence fully complementary to SEQ ID NO:1 under stringent conditions;
    a nucleotide sequence which hybridizes with SEQ ID NO:2 under stringent conditions; or
    a nucleotide sequence which hybridizes with a nucleotide sequence fully complementary to SEQ ID NO:2 under stringent conditions;
wherein stringent conditions are
    hybridizing for 16–18 hours at 65° C. in 6X SSC buffer containing 10% dextran sulfate, a 5X concentrated Denhardt's solution 10 mM EDTA, 0.05% SDS, 100 µg/ml denatured salmon sperm DNA;
    washing twice for 10 minutes at 65° C. in 2X SSC, once for 30 minutes at 65° C. in 2X SSC+0.1% SDS and once for 10 minutes at 65° C. in 0.1X SSC; and
    detecting hybridization to *C. jejuni* but not to other Campylobacter species.

2. A purified nucleotide sequence consisting of 12–20 contiguous nucleotides of a nucleic acid sequence selected from the group consisting of:
    a nucleotide sequence of SEQ ID NO:1;

a nucleotide sequence of SEQ ID NO:2;

a nucleotide sequence fully complementary to SEQ ID NO:1;

a nucleotide sequence fully complementary to SEQ ID NO:2;

a nucleotide sequence which hybridizes with SEQ ID NO:1 under stringent conditions;

a nucleotide sequence which hybridizes with a nucleotide sequence fully complementary to SEQ ID NO:1 under stringent conditions;

a nucleotide sequence which hybridizes with SEQ ID NO:2 under stringent conditions; or a nucleotide sequence which hybridizes with a nucleotide sequence fully complementary to SEQ ID NO:2 under stringent conditions;

wherein stringent conditions are hybridizing for 16–18 hours at 65° C. in 6X SSC buffer containing 10% dextran sulfate, a 5X concentrated Denhardt's solution 10 mM EDTA, 0.05% SDS, 100 µg/ml denatured salmon sperm DNA;

washing twice for 10 minutes at 65° C. in 2X SSC, once for 30 minutes at 65° C. in 2X SSC+0.1% SDS and once for 10 minutes at 65° C. in 0.1X SSC; and detecting hybridization to *C. jejuni* but not to other Campylobacter species.

3. A cloning vector comprising a nucleotide sequence selected from the group consisting of:

a nucleotide sequence of SEQ ID NO:1;

a nucleotide sequence of SEQ ID NO:2;

a nucleotide sequence fully complementary to SEQ ID NO:1;

a nucleotide sequence fully complementary to SEQ ID NO:2;

a nucleotide sequence which hybridizes with SEQ ID NO:1 under stringent conditions, a nucleotide sequence which hybridizes with a nucleotide sequence fully complementary to SEQ ID NO:1 under stringent conditions;

a nucleotide sequence which hybridizes with SEQ ID NO:2 under stringent conditions; or a nucleotide sequence which hybridizes with a nucleotide sequence fully complementary to SEQ ID NO:2 under stringent conditions;

wherein stringent conditions are hybridizing for 16–18 hours at 65° C. in 6X SSC buffer containing 10% dextran sulfate, a 5X concentrated Denhardt's solution 10 mM EDTA, 0.05% SDS, 100 µg/ml denatured salmon sperm DNA;

washing twice for 10 minutes at 65° C. in 2X SSC, once for 30 minutes at 65° C. in 2X SSC+0.1% SDS and once for 10 minutes at 65° C. in 0.1X SSC; and detecting hybridization to *C. jejuni* but not to other Campylobacter species.

4. A probe specific for a genomic nucleotide sequence of *Campylobacter jejuni*, comprising at least 12 contiguous nucleotides of a nucleic acid sequence selected from the group consisting of:

a nucleotide sequence of SEQ ID NO:1;

a nucleotide sequence of SEQ ID NO:2;

a nucleotide sequence fully complementary to SEQ ID NO:1;

a nucleotide sequence fully complementary to SEQ ID NO:2;

a nucleotide sequence which hybridizes with SEQ ID NO:1 under stringent conditions;

a nucleotide sequence which hybridizes with a nucleotide sequence fully complementary to SEQ ID NO:1 under stringent conditions;

a nucleotide sequence which hybridizes with SEQ ID NO:2 under stringent conditions; or a nucleotide sequence which hybridizes with a nucleotide sequence fully complementary to SEQ ID NO:2 under stringent conditions;

wherein stringent conditions are hybridizing for 16–18 hours at 65° C. in 6X SSC buffer containing 10% dextran sulfate, a 5X concentrated Denhardt's solution 10 mM EDTA, 0.05% SDS, 100 µg/ml denatured salmon sperm DNA;

washing twice for 10 minutes at 65° C. in 2X SSC, once for 30 minutes at 65° C. in 2X SSC+0.1% SDS and once for 10 minutes at 65° C. in 0.1X SSC; and detecting hybridization to *C. jejuni* but not to other Campylobacter species.

5. The probe according to claim 4 which is immobilized on a support.

6. A pair of oligonucleotide primers specific for the amplification of *Campylobacter jejuni*, wherein each primer consists of 18 to 30 contiguous nucleotides of a nucleic acid sequence selected from the group consisting of:

a nucleotide sequence of SEQ ID NO:1;

a nucleotide sequence of SEQ ID NO:2;

a nucleotide sequence fully complementary to SEQ ID NO:1;

a nucleotide sequence fully complementary to SEQ ID NO:2;

a nucleotide sequence which hybridizes with SEQ ID NO:1 under stringent conditions;

a nucleotide sequence which hybridizes with a nucleotide sequence fully complementary to SEQ ID NO:1 under stringent conditions;

a nucleotide sequence which hybridizes with SEQ ID NO:2 under stringent conditions; or a nucleotide sequence which hybridizes with a nucleotide sequence fully complementary to SEQ ID NO:2 under stringent conditions;

wherein stringent conditions are hybridizing for 16–18 hours at 65° C. in 6X SSC buffer containing 10% dextran sulfate, a 5X concentrated Denhardt's solution 10 mM EDTA, 0.05% SDS, 100 µg/ml denatured salmon sperm DNA;

washing twice for 10 minutes at 65° C. in 2X SSC, once for 30 minutes at 65° C. in 2X SSC+0.1% SDS and once for 10 minutes at 65° C. in 0.1X SSC; and detecting hybridization to *C. jejuni* but not to other Campylobacter species.

7. The pair of oligonucleotide primers of claim 6, wherein each primer consists of 18 to 22 contiguous nucleotides.

8. The pair of oligonucleotide primers of claim 6 which have the sequences of SEQ ID NO:3 and SEQ ID NO:4.

9. A method of detecting the presence of *Campylobacter jejuni* in a biological sample, comprising the steps of:

(a) contacting said biological sample with a pair of primers, wherein each primer consists of 18 to 30 contiguous nucleotides of a nucleic acid sequence selected from the group consisting of:

a nucleotide sequence of SEQ ID NO:1;

a nucleotide sequence of SEQ ID NO:2;

a nucleotide sequence fully complementary to SEQ ID NO:1;

a nucleotide sequence fully complementary to SEQ ID NO:2;

a nucleotide sequence which hybridizes with SEQ ID NO:1 under stringent conditions within a temperature range of (Tm—15° C.) to (Tm—20° C.);

a nucleotide sequence which hybridizes with a nucleotide sequence fully complementary to SEQ ID NO:1 under stringent conditions;

a nucleotide sequence which hybridizes with SEQ ID NO:2 under stringent conditions; or a nucleotide sequence which hybridizes with a nucleotide sequence fully complementary to SEQ ID NO:2 under stringent conditions;

wherein stringent conditions are hybridizing for 16–18 hours at 65° C. in 6X SSC buffer containing 10% dextran sulfate, a 5X concentrated Denhardt's solution 10 mM EDTA, 0.05% SDS, 100 μg/ml denatured salmon sperm DNA;

washing twice for 10 minutes at 65° C. in 2X SSC, once for 30 minutes at 65° C. in 2X SSC+0.1% SDS and once for 10 minutes at 65° C. in 0.1X SSC; and detecting hybridization to *C. jejuni* but not to other Campylobacter species;

(b) amplifying any genomic nucleic acid sequences of *Campylobacter jejuni* in said sample; and (c) detecting the presence of any amplified genomic nucleic acid sequences.

10. The method of claim 9, further comprsiing the step of (d) verifying that the sequence of any amplified genomic nucleoic acid sequences correspond to genomic material of *Campylobacter jejuni*.

11. The method of claim 10, wherein said verifying comprises hybridizing said amplified nucleic acid sequence with a probe specific for *Campylobacter jejuni*, sequencing said amplified nucleic acid sequence or mapping the sequence of said amplified nucleic acid sequence by restriction site analysis.

12. A method of detecting the presence of *Campylobacter jejuni* in a food sample, comprising the steps of:

(a) low speed centrifuging said food sample to remove coarse organic food debris, (b) contacting the food sample with a pair of primers, wherein each primer consists of 18 to 30 consecutive nucleotides of a nucleic acid sequence selected from the group consisting of:

a nucleotide sequence of SEQ ID NO:1;

a nucleotide sequence of SEQ ID NO:2;

a nucleotide sequence fully complementary to SEQ ID NO:1;

a nucleotide sequence fully complementary to SEQ ID NO:2;

a nucleotide sequence which hybridizes with SEQ ID NO:1 under stringent conditions;

a nucleotide sequence which hybridizes with a nucleotide sequence fully complementary to SEQ ID NO:1 under stringent conditions;

a nucleotide sequence which hybridizes with SEQ ID NO:2 under stringent conditions; or a nucleotide sequence which hybridizes with a nucleotide sequence fully complementary to SEQ ID NO:2 under stringent conditions;

wherein stringent conditions are hybridizing for 16–18 hours at 65° C. in 6X SSC buffer containing 10% dextran sulfate, a 5X concentrated Denhardt's solution 10 mM EDTA, 0.05% SDS, 100 μg/ml denatured salmon sperm DNA;

washing twice for 10 minutes at 65° C. in 2X SSC, once for 30 minutes at 65° C. in 2X SSC+0.1% SDS and once for 10 minutes at 65° C. in 0.1X SSC; and detecting hybridization to *C. jejuni* but not to other Campylobacter species;

(c) amplifying any genomic nucleic acid sequences of *Campylobacter jejuni* in said sample; and (d) detecting the presence of any amplified genomic nucleic acid sequences.

13. A kit for detecting the presence of *Campylobacter jejuni* in a biological or food sample, comprising:

(a) a pair of primers, wherein each primer consists of 18 to 30 contiguous nucleotides of a nucleic acid sequence selected from the group consisting of:

a nucleotide sequence of SEQ ID NO:1;

a nucleotide sequence of SEQ ID NO:2;

a nucleotide sequence fully complementary to SEQ ID NO:1;

a nucleotide sequence fully complementary to SEQ ID NO:2;

a nucleotide sequence which hybridizes with SEQ ID NO:1 under stringent conditions;

a nucleotide sequence which hybridizes with a nucleotide sequence fully complementary to SEQ ID NO:1 under stringent conditions;

a nucleotide sequence which hybridizes with SEQ ID NO:2 under stringent conditions; or a nucleotide sequence which hybridizes with a nucleotide sequence fully complementary to SEQ ID NO:2 under stringent conditions;

wherein stringent conditions are hybridizing for 16–18 hours at 65° C. in 6X SSC buffer containing 10% dextran sulfate, a 5X concentrated Denhardt's solution 10 mM EDTA, 0.05% SDS, 100 μg/ml denatured salmon sperm DNA;

washing twice for 10 minutes at 65° C. in 2X SSC, once for 30 minutes at 65° C. in 2X SSC+0.1% SDS and once for 10 minutes at 65° C. in 0.1X SSC; and detecting hybridization to *C. jejuni* but not to other Campylobacter species; and (b) reagents necessary for amplifying genomic nucleic acid sequences of *Campylobacter jejuni*.

14. The kit of claim 13, further comprising:

(c) a standard which is a probe comprising at least 12 consecutive nucleotides of a nucleic acid sequence selected from the group consisting of:

a nucleotide sequence of SEQ ID NO:1;

a nucleotide sequence of SEQ ID NO:2;

a nucleotide sequence fully complementary to SEQ ID NO:1;

a nucleotide sequence fully complementary to SEQ ID NO:2;

a nucleotide sequence which hybridizes with SEQ ID NO:1 under stringent conditions;

a nucleotide sequence which hybridizes with a nucleotide sequence fully complementary to SEQ ID NO:1 under stringent conditions;

a nucleotide sequence which hybridizes with SEQ ID NO:2 under stringent conditions; or a nucleotide sequence which hybridizes with a nucleotide sequence fully complementary to SEQ ID NO:2 under stringent conditions;

wherein stringent conditions are hybridizing for 16–18 hours at 65° C. in 6X SSC buffer containing 10% dextran sulfate, a 5X concentrated Denhardt's solution 10 mM EDTA, 0.05% SDS, 100 µg/ml denatured salmon sperm DNA;

washing twice for 10 minutes at 65° C. in 2X SSC, once for 30 minutes at 65° C. in 2X SSC+0.1% SDS and once for 10 minutes at 65° C. in 0.1X SSC; and detecting hybridization to *C. jejuni* but not to other Campylobacter species.

15. A method for the epidemiological locating and classification of identical *Campylobacter jejuni* strains and the establishment of links as to their source and the propagation of an infection, said method comprising measuring the repetitiveness in said *Campylobacter jejuni* strain's genome of a nucleic acid sequence corresponding to the sequence of a probe comprising at least 12 contiguous nucleotides of a nucleic acid sequence selected from the group consisting of:

a nucleotide sequence of SEQ ID NO:1;

a nucleotide sequence of SEQ ID NO:2;

a nucleotide sequence fully complementary to SEQ ID NO:1;

a nucleotide sequence fully complementary to SEQ ID NO:2;

a nucleotide sequence which hybridizes with SEQ ID NO:1 under stringent conditions;

a nucleotide sequence which hybridizes with a nucleotide sequence fully complementary to SEQ ID NO:1 under stringent conditions;

a nucleotide sequence which hybridizes with SEQ ID NO:2 under stringent conditions; or a nucleotide sequence which hybridizes with a nucleotide sequence fully complementary to SEQ ID NO:2 under stringent conditions;

wherein stringent conditions are hybridizing for 16–18 hours at 65° C. in 6X SSC buffer containing 10% dextran sulfate, a 5X concentrated Denhardt's solution 10 mM EDTA, 0.05% SDS, 100 µg/ml denatured salmon sperm DNA;

washing twice for 10 minutes at 65° C. in 2X SSC, once for 30 minutes at 65° C. in 2X SSC+0.1% SDS and once for 10 minutes at 65° C. in 0.1X SSC; and detecting hybridization to *C. jejuni* but not to other Campylobacter species.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:

( A ) LENGTH: 147 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Campylobacter jejuni ( v i i ) IMMEDIATE SOURCE:
( B ) CLONE: VS2

( x i ) SEQUENCE DESCRIPTION: SEQ ID NO: 1:

| | | | | | |
|---|---|---|---|---|---|
| AAGCTTGTGA | TACTTTTAAG | TGCTATAGAA | AGTGAAAATG | AAATTTCTTT | AGCAGGCATA | 60
| TATAGAGCGT | ATTGTTCCAA | ATTTGATTTA | AAGAATGAAA | TTTTAGAATG | GGGTCTTAAA | 120
| ATATTTAAAA | ACAATAATGC | CTTAAAA | | | | 147

( 2 ) INFORMATION FOR SEQ ID NO: 2:

( i ) SEQUENCE CHARACTERISTICS:
( A ) LENGTH: 1189 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Campylobacter jejuni ( v i i ) IMMEDIATE SOURCE:
( B ) CLONE: VS1

( x i ) SEQUENCE DESCRIPTION: SEQ ID NO: 2:

| | | | | | |
|---|---|---|---|---|---|
| AAGCTTGTGA | TACTTTTAAG | TGCTATAGAA | AGTGAAAATG | AAATTTCTTT | AGCAGGCATA | 60
| TATAGAGCGT | ATTGTTCCAA | ATTTGATTTA | AAGAATGAAA | TTTTAGAATG | GGGTCTTAAA | 120
| ATATTTAAAA | ACAATAATGC | CTTAAAAGAT | CTTGTAGAAA | AAGAAGATAT | ATACAATCCT | 180
| ATTGTTGTAA | GTAGTTTGGT | TTCTAAGCTA | GAAAATTTAG | AAAATTTAGA | GCTTTTATAT | 240
| ACTTTAACTT | GGCTAAAGGC | TAAGGCTTTA | AATTATAATG | CTTTTTATTT | TAGAGTTCTT | 300
| GATAAACTTT | TAGAAAATGC | AAAACAAGGT | TTTGAAGATG | AAAATCTACT | TGAAGAAAGT | 360
| GCAAGAAGGG | TAAAAAAAGA | ATTAACACTT | AAAAGAAGTA | AGATTTTTTT | AGAGCAAGAT | 420
| GAAATTTTGC | AGGATAAAAT | CATACATATC | AAATCAAATC | TTTTTATTAT | AAAAAATACT | 480
| TTTGAAGATA | TTGTTATGAT | TTCTAAATTA | GCCAAAGAAA | ATGATTTTAA | ATTTTGGTTT | 540
| AGTAATGAAA | CAAATCTTAG | TTTGCAAATT | GTTGCACCAC | TTCATTTTAA | TATTGCCATT | 600
| ATTTTAAGTT | CTTTAACAAA | TTTAAATCTT | ATTTTTATGA | ATTTTTTGA | ACTTTTTGAT | 660
| GATAAAATTT | ATTTAAGGTT | TGAATATGAT | AATATTATCA | GTGATGAGCA | AAAACTAAAA | 720
| CTTTGTGAGC | TTTTAAATTC | AAATCTTTCT | GGTTTTAATT | TGAAAAAAAT | TAAAAAGCCA | 780
| ATCATTAAAA | AAGAGGAGTT | AAAATTAGAC | TTAAACTATT | CTAAAATGTA | TGCCAAATTA | 840
| GGTCTTAATA | CTAAAGATCA | GCAAGGTTTA | ATGGCGTATT | TGATGAATGT | TTTAATGAA | 900
| CTTGAACTTG | TTTTATGTGC | AGCAAAAATT | CAAACCATAA | GACAAAGGAC | GCGTAATATT | 960

| | | | | | | |
|---|---|---|---|---|---|---|
| TTTATTTTTC | AAAAGAATGA | AAAATTAGAA | CATAGCGAGC | AAAAGTTAGT | TAATTTATTA | 1020 |
| ATAAGTGAGT | AAAAAAATGT | GTGGAATCGT | AGGCTATATA | GGAAATAATG | AAAAAAAACA | 1080 |
| AATTATACTA | AATGGACTTA | AAGAATTAGA | ATATCGTGGC | TATGATAGTG | CGGGTATGGC | 1140 |
| AGTGATGCAA | GAAGGCGAAC | TTAGTTTTTT | TAAAGCTGTA | GGAAAGCTT | | 1189 |

( 2 ) INFORMATION FOR SEQ ID NO: 3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: Campylobacter jejuni     ( v i i ) IMMEDIATE SOURCE:
        ( B ) CLONE: OligoVS15

( x i ) SEQUENCE DESCRIPTION: SEQ ID NO: 3:

GAATGAAATT TTAGAATGGG G        21

( 2 ) INFORMATION FOR SEQ ID NO: 4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: Campylobacter jejuni     ( v i i ) IMMEDIATE SOURCE:
        ( B ) CLONE: OligoVS16

( x i ) SEQUENCE DESCRIPTION: SEQ ID NO: 4:

GATATGTATG ATTTATCCT GC        22